US00PP32952P3

(12) United States Plant Patent
Knapp et al.

(10) Patent No.: US PP32,952 P3
(45) Date of Patent: Apr. 6, 2021

(54) STRAWBERRY PLANT NAMED 'UCD ROYAL ROYCE'

(50) Latin Name: ***Fragaria* x *ananassa* Duchesne**
Varietal Denomination: UCD Royal Royce

(71) Applicant: The Regents of the University of California, Oakland, CA (US)

(72) Inventors: Steven J. Knapp, Davis, CA (US); Glenn S. Cole, Davis, CA (US); Douglas V. Shaw, Davis, CA (US); Kirk D. Larson, Santa Ana, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/501,374

(22) Filed: Apr. 1, 2019

(65) Prior Publication Data

US 2019/0380245 P1 Dec. 12, 2019
US 2020/0187402 P9 Jun. 11, 2020

Related U.S. Application Data

(60) Division of application No. 15/932,994, filed on Jun. 7, 2018, which is a continuation of application No. 15/530,135, filed on Dec. 6, 2016, now abandoned, which is a continuation of application No. 14/545,653, filed on Jun. 3, 2015, now abandoned.

(60) Provisional application No. 61/999,632, filed on Jul. 30, 2014, provisional application No. 61/997,548, filed on Jun. 4, 2014.

(51) Int. Cl.
*A01H 5/08* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./209
CPC ..... A01H 6/7409
See application file for complete search history.

*Primary Examiner* — Anne Marie Grunberg
(74) *Attorney, Agent, or Firm* — Kilpatrick Townsend & Stockton LLP

(57) ABSTRACT

'UCD Royal Royce' is a day-neutral cultivar of a strawberry plant that provides high yields and produces fewer runners that many high-yielding day-neutral cultivars.

7 Drawing Sheets

Genus and species: The strawberry cultivar of this invention is botanically identified as *Fragaria* x *ananassa* Duchesne.

Variety denomination: The variety denomination is 'UCD Royal Royce'.

BACKGROUND OF THE INVENTION

This invention relates to a new and distinct day-neutral strawberry cultivar designated as 'UCD Royal Royce', which originated from a cross performed in the winter of 2008 between proprietary germplasm parents 03C114P003 (unpatented) and 04C009P005 (unpatented). Seeds of the cross were harvested from greenhouse-grown plants in the spring of 2008 and germinated in June 2008. Seedlings were transplanted to a greenhouse in July 2008 and transplanted to the field in October 2008. 'UCD Royal Royce' was selected and clones were first harvested in 2009. 'UCD Royal Royce' has been asexually propagated since 2009.

The plant of this selection was originally designated '08C123P001' (also represented as 8.123-1) and later called '16DN009' or 'UC9' for evaluation in field trials.

BRIEF SUMMARY OF THE INVENTION

'UCD Royal Royce' is a day-neutral (ever-bearing) strawberry cultivar selected for increased marketable fruit yield, extended shelf-life and decreased runner (stolon) production. 'UCD Royal Royce' consistently produces more marketable fruit per hectare, particularly during the first six to seventh months of an eight or nine-month harvest season, compared to San Andreas (U.S. Plant Pat. No. 19,975), 'Monterey' (U.S. Plant Pat. No. 19,767) or 'Cabrillo' (U.S. Plant Pat. No. 27,830); and has fewer stolons (runners) than 'Monterey' or 'Cabrillo'. 'UCD Royal Royce' also delivers yield earlier than cultivar 'UCD Moxie' (U.S. Plant patent application Ser. No. 16/501,376), whereas the cumulative marketable fruit yield of 'UCD Moxie' surpasses that of 'UCD Royal Royce' late in the season. 'UCD Royal Royce' is day neutral compared to short day parent 4C009P005, and exhibits earlier flowering and increased numbers of stolons compared to parent 03114P003.

'UCD Royal Royce' was genotyped with a 35,000-SNP array (Hardigan et. al., *Plant Genome* 11:180049, 2018). The variety has a unique DNA profile compared to 'Cabrillo', 'Monterey', 'UCD Moxie', and 'UCD Valiant' (U.S. Plant patent application Ser. No. 16/501,375). The pairwise genetic distances between 'UCD Royal Royce' and 'UCD Valiant', 'UCD Moxie', 'Cabrillo', and 'Monterey' are estimated to be 0.270, 0.167, 0.259, and 0.302, respectively based on the 35,000-SNP genotype analysis. 'UCD Royal Royce' also has a unique DNA profile compared to each of its parents, proprietary germplasm varieties 03C114P003 and 04C009P005.

'UCD Royal Royce' is maintained by annual asexual propagation by stolons in Winters, Calif.

BRIEF DESCRIPTION OF THE DRAWINGS

The colors in the photograph are depicted as nearly true as is reasonably possible to obtain in color reproductions of this type.

DETAILED DESCRIPTION OF THE INVENTION

Fruit Production

Figure 1:
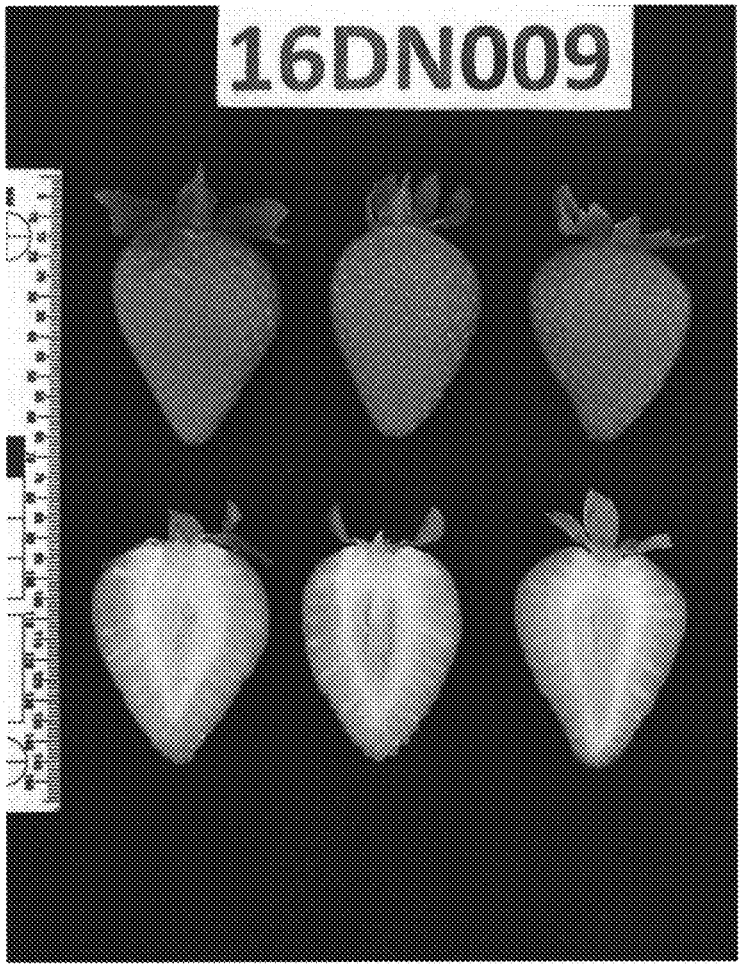
FIG. 1 shows fruit of 'UCD Royal Royce' in cross-section.
Figure 2:
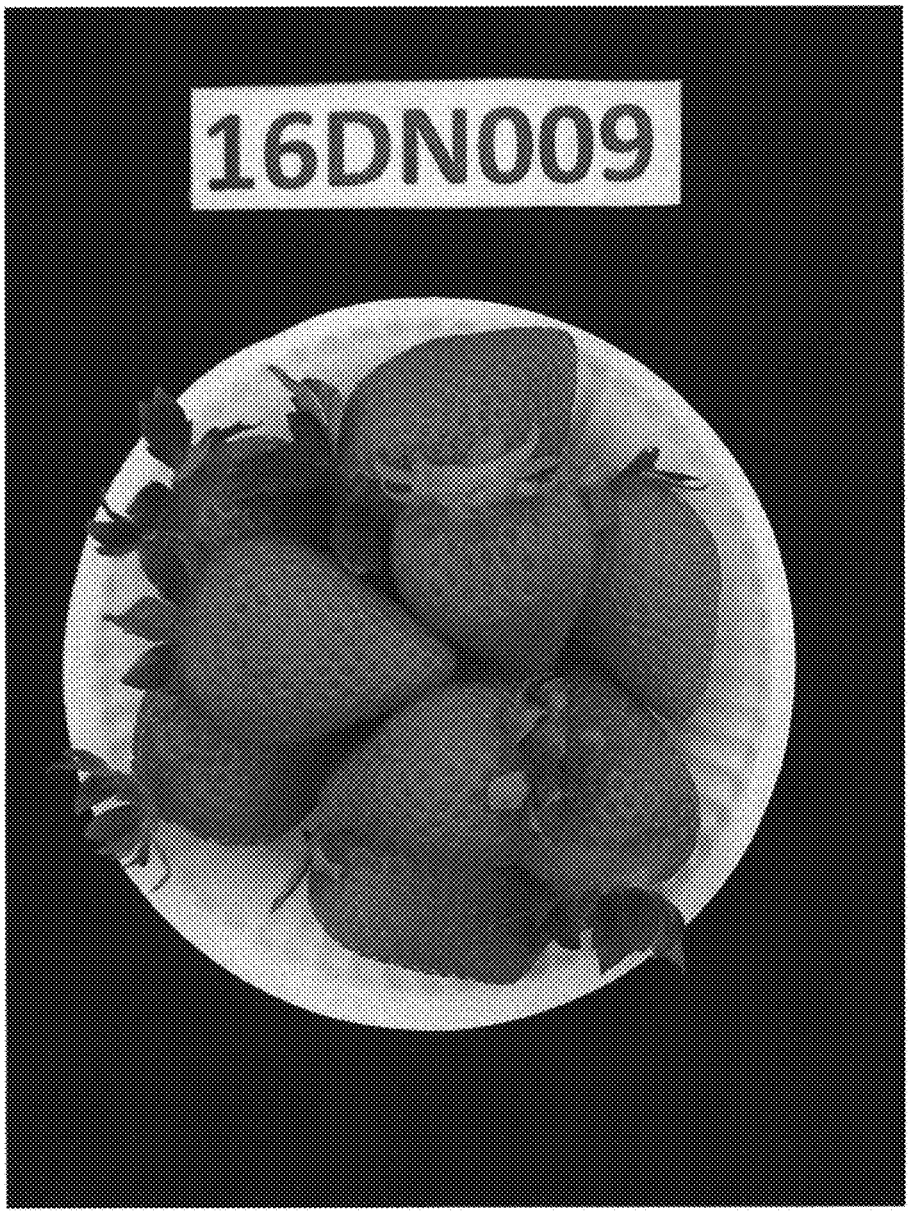
FIG. 2 illustrates color of the fruit.
Figure 3:
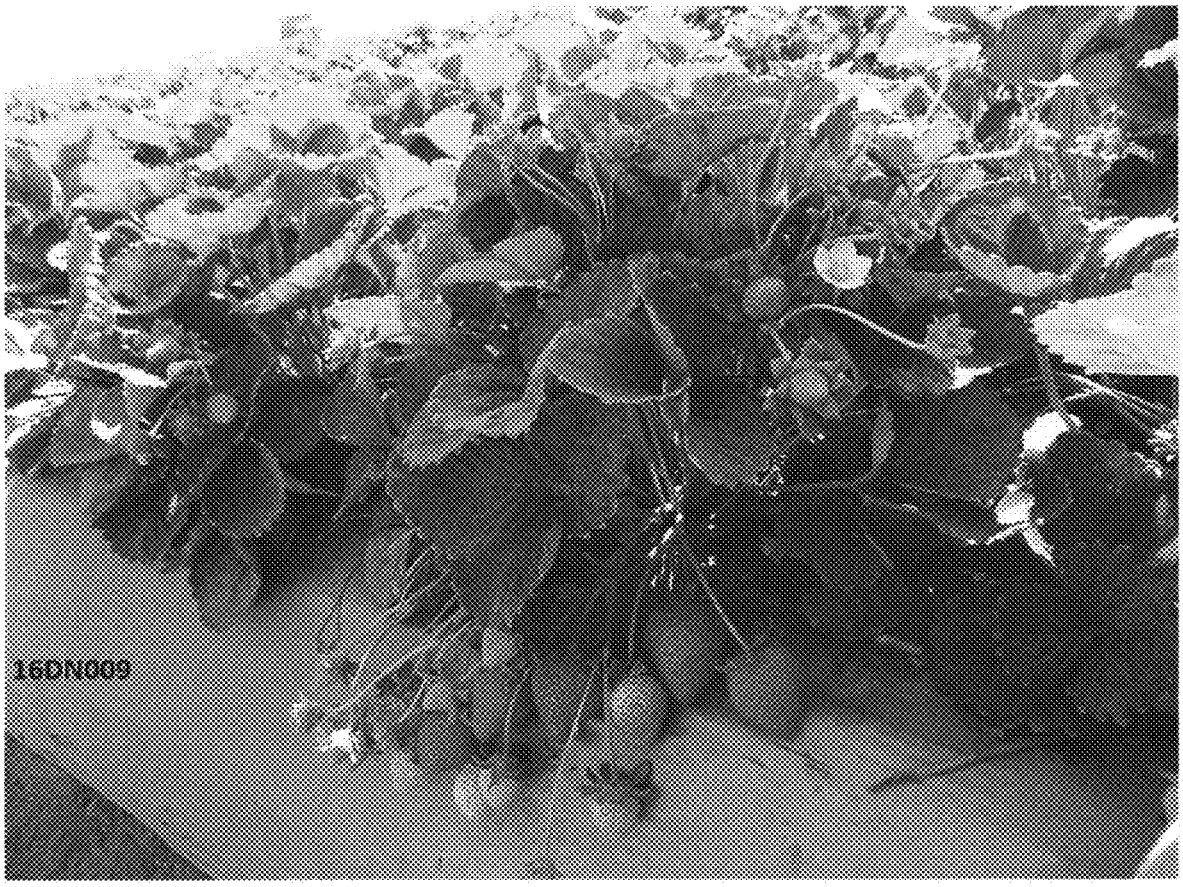
FIG. 3 depicts general flowering and fruiting characteristics of 'UCD Royal Royce'.
Figure 4:
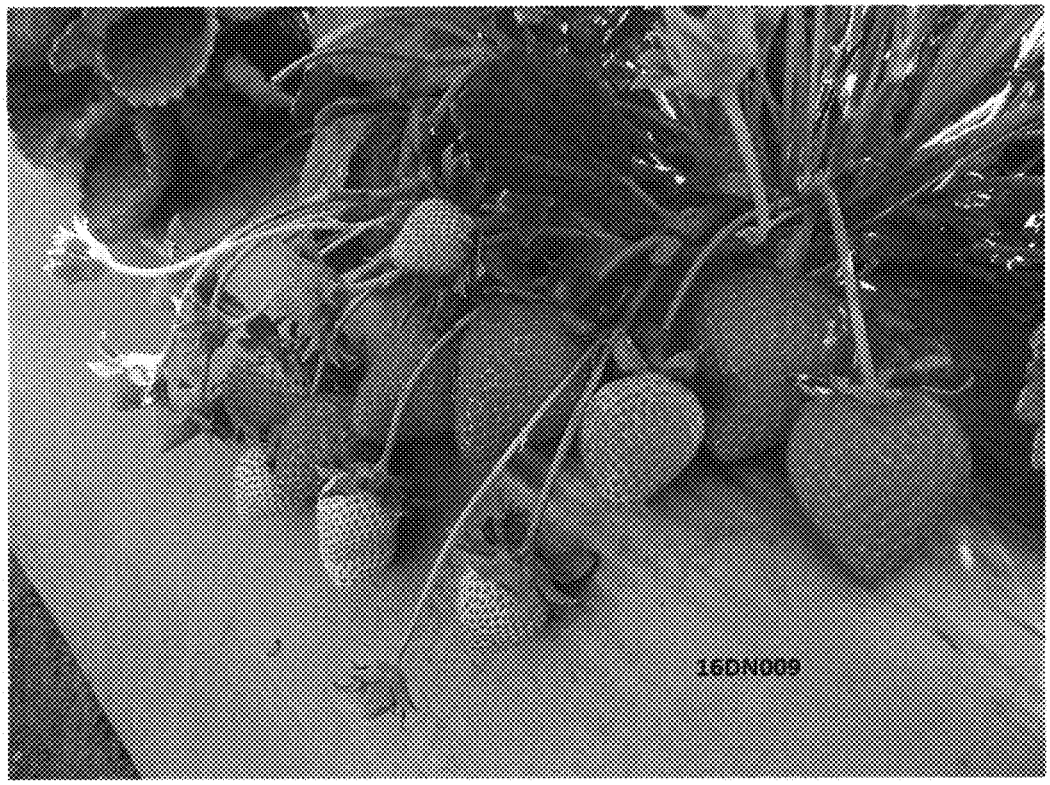
FIG. 4 shows representative fruit trusses of the plant.
Figure 5:
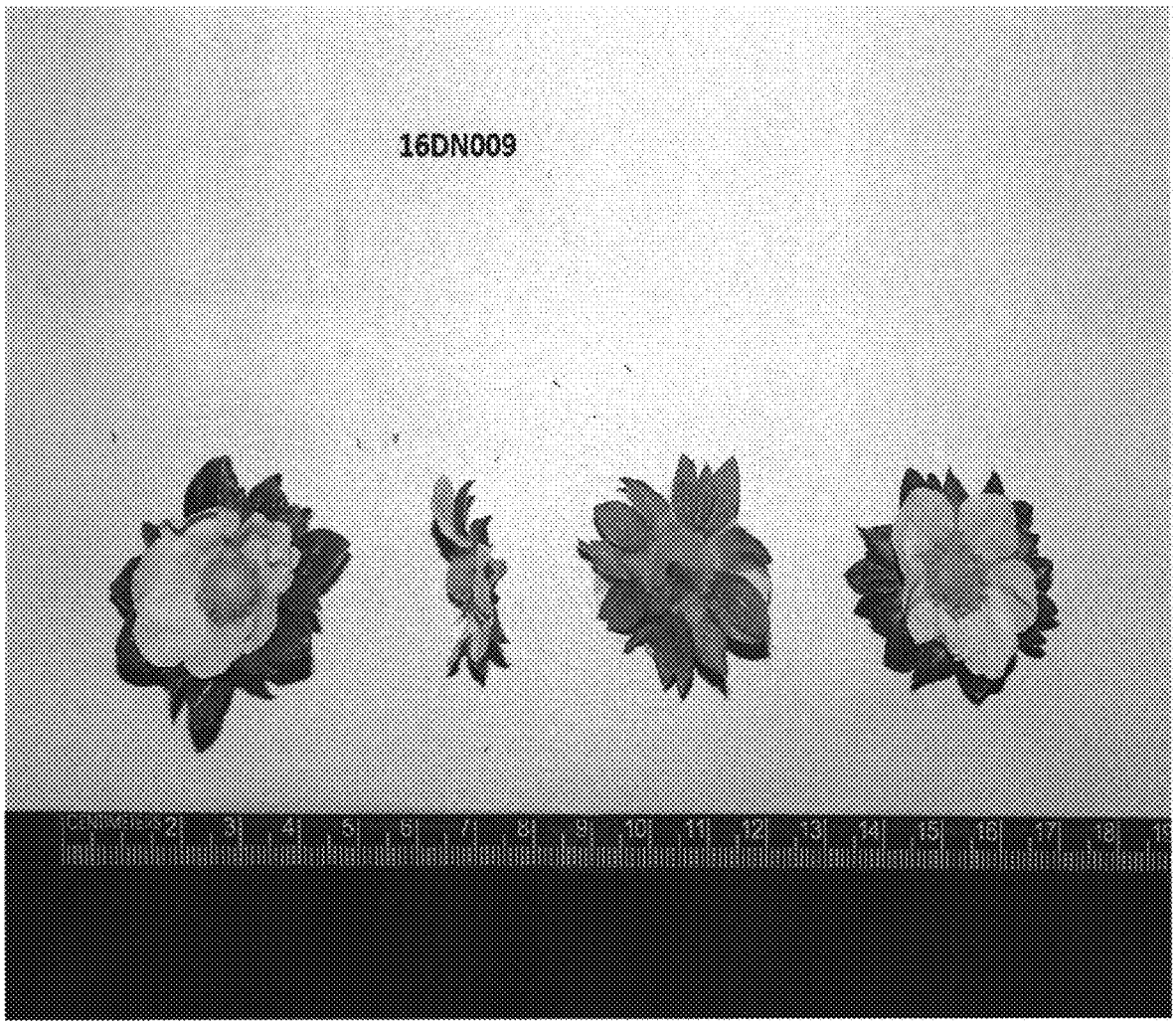
FIG. 5 shows representative flowers of the plant.
Figure 6:
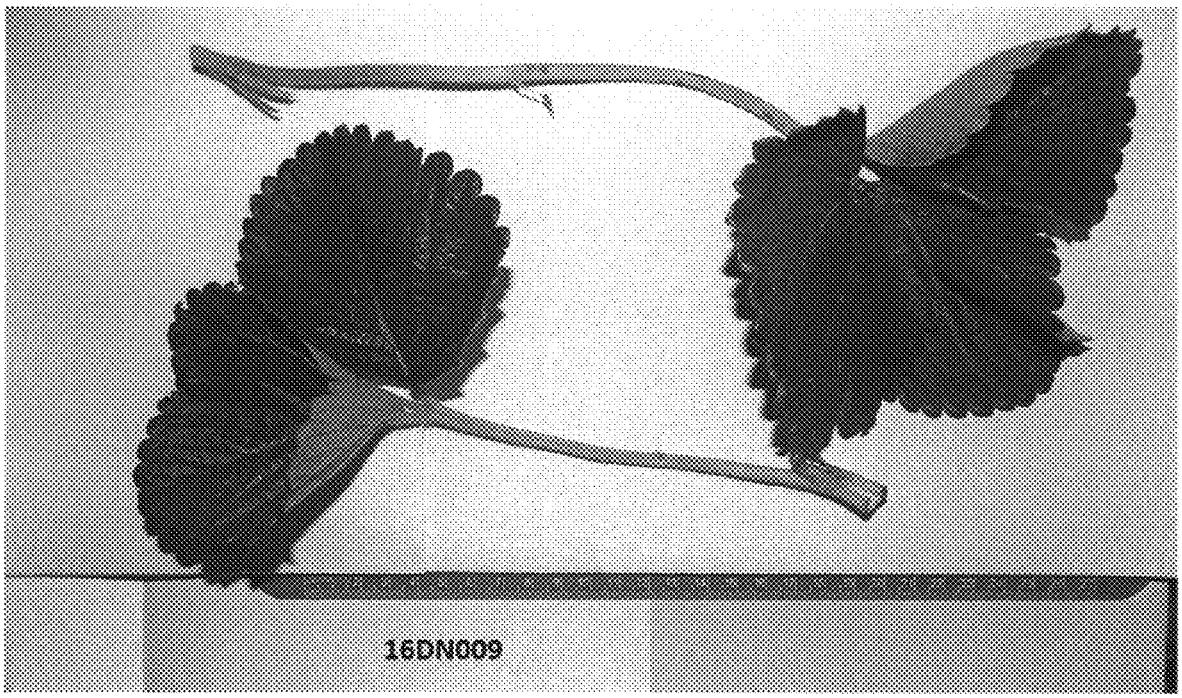
FIG. 6 shows representative leaves of the plant.
Figure 7:
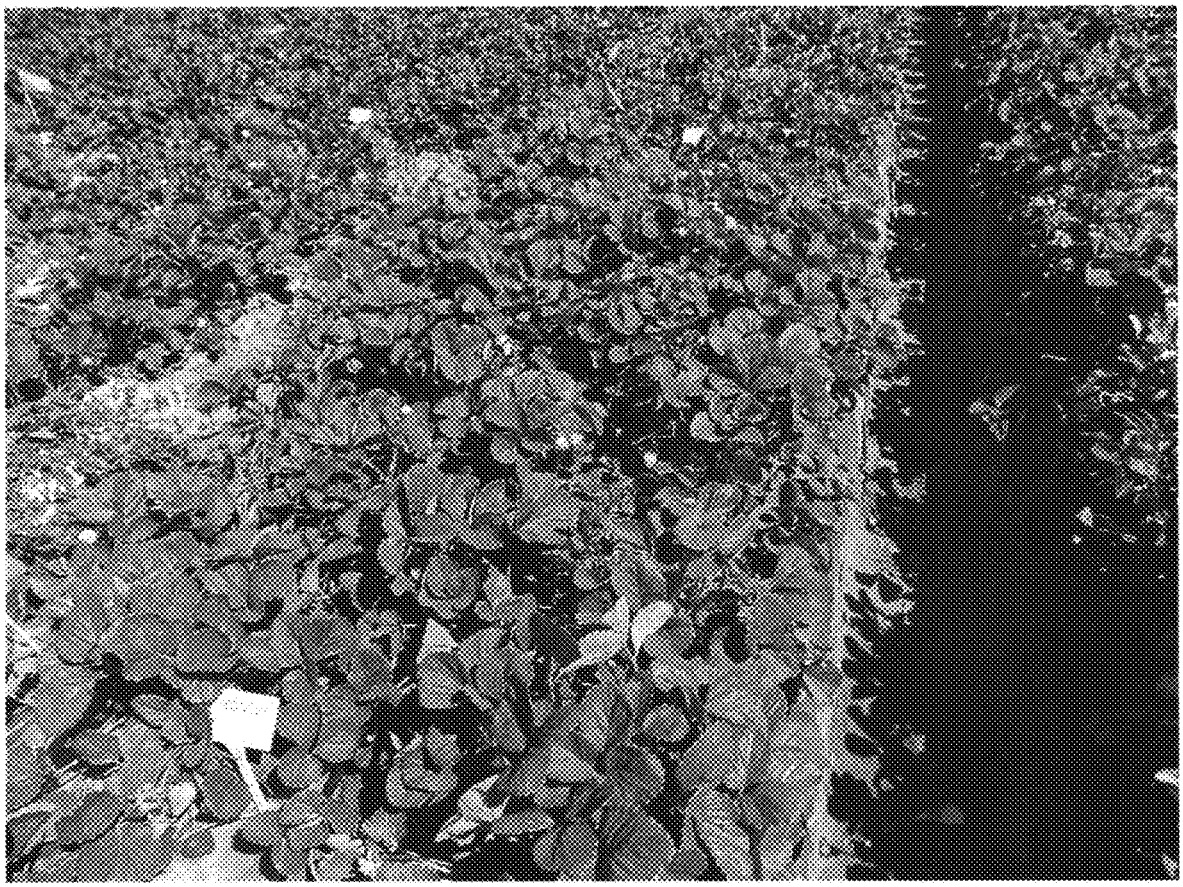
FIG. 7 depicts plant habit.

'UCD Royal Royce' and comparison cultivars were asexually propagated in high-elevation nurseries in Dorris and Mcdoel, Calif. for field testing in 2015-2016, 2016-2017, and 2017-2018. Clones were harvested according to commercial planting schedules, which were calibrated by the number of chill hours required for optimum production in Santa Maria and Prunedale, Calif.

Cultivar testing in small-plot yield trials was performed as follows. Test day-neutral cultivars and comparison cultivars were field tested in Oso Flaco (Santa Maria, Calif.) and Prunedale, Calif. in 2015-2016. Fruit was harvested once or twice per week over the spring and summer growing season: March 16 to Aug. 18, 2016 in Santa Maria (31 harvests) and April 2 to Aug. 27, 2016 in Prunedale (30 harvests). 'UCD Royal Royce' was selected on the basis of fruit appearance, size, shelf-life, and cumulative marketable fruit yield for a second year (2016-17) of replicated testing in Santa Maria and Prunedale (Tables 1-2). Fruit was harvested once or twice per week over the growing season: March 13 to Aug. 21, 2017 in Santa Maria (25 harvests) and April 3 to Sep. 1, 2017 in Prunedale (44 harvests in Prunedale). To highlight differences among cultivars, the yield data were displayed in three ways: (a) per plant yields for individual harvests for each location×year combination for 'UCD Royal Royce', 'Monterey', 'San Andreas', and 'Cabrillo'; (b) per plant cumulative marketable yields for 'UCD Royal Royce', 'Monterey', 'San Andreas', and 'Cabrillo'; and (c) per plant cumulative marketable yields tested in both years and locations. Entry ranks were highly consistent and the best and worst performing cultivars were virtually identical over locations and years.

Table 1 shows marketable yield (g/plant) for 'UCD Royal Royce' compared to that for 'Monterey', 'San Andreas', and 'Cabrillo' tested in small-plot yield trials in Santa Maria, Calif. and Prunedale, Calif. in 2015-16 and 2016-17.

Table 2 shows the range in increase in yield compared to 'Monterey', 'San Andreas', and 'Cabrillo' for the small-plot yield trials.

TABLE 1

Least-square means for cumulative marketable yield tested in small-plot yield trials in Santa Maria, CA and Prunedale, CA in 2015-2016 and 2016-2017

| | Santa Maria | | Prunedale | | Yield across Locations and Years |
|---|---|---|---|---|---|
| Cultivar | 2015-16 | 2016-17 | 2015-16 | 2016-17 | (g/plant) |
| UCD Royal Royce | 2,016 | 2,329 | 1,750 | 2,632 | 2,183 |
| Cabrillo | 1,617 | 2,073 | 1,362 | 2,299 | 1,838 |
| Monterey | 1,115 | 1,324 | 1,077 | 1,722 | 1,310 |
| San Andreas | 1,229 | 1,096 | 1,048 | 1,569 | 1,236 |

TABLE 2

Least-square means for cumulative marketable yield (g/plant) across years and locations tested in the small-plot yield trials in Santa Maria and Prunedale. The ranges for yield increases over comparison cultivars were estimated from least square means for individual environments (see, Table 1). (Percent Marketable Fruit = (Cumulative Marketable Fruit Yield)/(Cumulative Total Fruit Yield)

| Cultivar | Yield (g/plant) | Percent Market-able Fruit | Yield Increase Range Over San Andreas | Yield Increase Range Over Monterey | Yield Increase Range Over Cabrillo |
|---|---|---|---|---|---|
| UCD Royal Royce | 2,183 | 87-88 | 64-112% | 53-81% | 12-28% |
| Cabrillo | 1,838 | 86-87 | | | |
| Monterey | 1,310 | 79-82 | | | |
| San Andreas | 1,236 | 76-84 | | | |

The cumulative marketable fruit yields of 'UCD Royal Royce' were significantly greater than 'Cabrillo' ($p<0.0078$), 'Monterey' ($p<0.0001$), and 'San Andreas' ($p<0.0001$) across years and locations (Table 1). The per plant yields of 'UCD Royal Royce' were 12 to 112% greater than 'Cabrillo', 'Monterey', and 'San Andreas' (Table 2). The mean fruit size for 'UCD Royal Royce' (29.7 g/fruit) was not significantly different from 'Cabrillo' (30.0 g/fruit; $p=0.78$) or Monterey (28.4 g/fruit $p=0.23$), but was significantly greater than 'San Andreas' (26.7 g/fruit; $p=0.007$).

The marketable fruit percentages for 'UCD Royal Royce' and 'Cabrillo' were comparable (86-88%) and superior to 'Monterey' and 'San Andreas' (76 to 84%) (Table 2).

Significantly less runner production was observed in 'UCD Royal Royce' compared to the other high yielding cultivars tested in small-plot yield trials. Runner production differences among cultivars could not be absolutely quantified because growers trimmed runners to prevent the diversion of energy away from fruit production; however, it is estimated based on observation that runner production was reduced by at least 50% for 'UCD Royal Royce' compared to runner production by 'San Andreas', 'Monterey', and 'Cabrillo'. This was confirmed in large-plot yield trials described below.

'UCD Royal Royce' was selected, with other test varieties, for advanced testing in large-plot yield trials (150 plants/plot) with five commercial growers in 2017-18. The selection criteria were: high cumulative marketable yields, high marketable fruit percentages, resistance to bruising and deterioration with harvest, handling, and storage, fruit appearance, and reduced runner production in coastal production environments. The production systems for large-plot yield trials were diverse and included: low-input organic (Santa Maria, Calif.), low-input fumigated (Salinas, Calif.), and high-input fumigated (Oso Flaco, Calif., Prunedale, Calif. and Moss Landing, Calif.). Fruit was harvested from February 2 to October 5 in Oso Flaco (52 harvests), April 3 to October 4 in Santa Maria (53 harvests), April 12 to October 6 in Prunedale (48 harvests), May 7 to October 8 in Moss Landing (45 harvests), and March 9 to October 12 in Salinas (36 harvests). The residual for statistical analyses was the entry×location interaction mean square.

TABLE 3

Least square means for cumulative marketable fruit yield (cartons/acre) for 'UCD Royal Royce', 'Monterey', and 'Cabrillo' grown in unreplicated large-plot (150 plant) yield trials in five locations in 2017-18, where a carton = eight clamshells and eight clamshells/carton × one pound/clamshell = eight pounds/carton.

| Cultivar | Salinas | Santa Maria | Oso Flaco | Prune-dale | Mossing Landing | Across Locations |
|---|---|---|---|---|---|---|
| UCD Royal Royce | 8,729 | 11,042 | 16,837 | 15,069 | 10,603 | 12,456 |
| Cabrillo | 5,201 | 6,892 | 17,569 | 14,057 | 9,465 | 10,637 |
| Monterey | NA | 7,891 | 14,731 | 11,940 | 10,257 | 10,274 |

TABLE 4

Least square means for fruit weight (g/fruit) for 'UCD Royal Royce', 'Monterey', and 'Cabrillo' grown in unreplicated large-plot (150 plant) yield trials in in five locations in 2017-18, where fruit weight = (weight of fruit per clamshell)/(number of fruit per clamshell).

| Cultivar | Salinas | Santa Maria | Oso Flaco | Prune-dale | Mossing Landing | Across Locations |
|---|---|---|---|---|---|---|
| UCD Royal Royce | 25.0 | 21.8 | 28.5 | 28.6 | 34.1 | 27.6 |
| Cabrillo | 26.1 | 21.9 | 28.0 | 27.5 | 34.0 | 27.5 |
| Monterey | NA | 21.6 | 29.4 | 27.9 | 33.8 | 27.8 |

TABLE 5

Statistical significance (Pr > F) of differences between least square means for cumulative fruit yield (cartons/acres) and fruit weight (g/fruit) for 'UCD Royal Royce', 'Monterey', and 'Cabrillo' tested in unreplicated large-plot (150 plant) yield trials in five locations in 2017-18.

| | Yield | | Fruit Weight (g/fruit) | |
|---|---|---|---|---|
| Comparison | Difference (carton/acre) | Pr > F | Difference (g/fruit) | Pr > F |
| UCD Royal Royce-Monterey | 2,182 | 0.0392 | −0.22 | 0.6631 |
| OCD Royal Royce-Cabrillo | 1,820 | 0.0610 | 0.11 | 0.8133 |

The mean cumulative marketable yields 'UCD Royal Royce' was 12,456 cartons/acre=99,648 pounds/acre across production systems and locations (Table 3). Reduced runner production was observed for 'UCD Royal Royce' across trials. 'UCD Royal Royce' was the highest yielding cultivar through August, 2018 compared to 'Monterey', 'Cabrillo', and two other test cultivars (data not shown), and second highest yielding cultivar through October, 2018 compared to 'Monterey', 'Cabrillo' (Table 3) and two other test cultivars (data not shown). The cumulative marketable fruit yields of (Table 3) were significantly greater than 'Monterey' (p=0.039) and 'Cabrillo' (p=0.061) (Table 5). 'UCD Royal Royce' produced 1,820 cartons/acre (11,144 pounds/acre) more than 'Cabrillo' and 2,182 cartons/acre (17,464 pounds/acre) more than 'Monterey' (Tables 3 & 5). 'UCD Royal Royce' fruit weights were not significantly different from 'Monterey' (p=0.49) or 'Cabrillo' (p=0.46) (Tables 4 & 5).

To assess the quality of freshly harvested fruit, firmness (grams force), total soluble solids (SS) concentration, and titratable acid (TA) concentrations were measured from samples of fruit harvested on three dates from each location in 2017-18 (Tables 6-7). Harvest dates were one month apart with one replication per harvest date, 10 sub-samples per replication for firmness, and three subsamples per replication for SS and TA. Firmness was quantified with a hand-held penetrometer measuring the grams of force needed to puncture the fruit. SS and TA concentrations were quantified with benchtop instruments. The SS to TA ratio provides a relative measure of sweetness. To assess shelf-life, fruit weight (g/clamshell), SS, brightness (ordinal scale with 1=excellent to 5=unmarketable), liquid leakage (g/clamshell), and mold incidence (%) were quantified from samples of fruit harvested on two dates from each location with fruit stored under standard 4° C. conditions for 0, 7, 14, and 21 days (Table 8). Harvest dates were one month apart with one replication per harvest date.

TABLE 6

Least-square means (LSMs) for firmness, soluble solids concentration (SS), and titratable acid concentration (TA) for 'UCD Royal Royce', 'Monterey', and 'Cabrillo' grown in five locations in 2017-18. LSMs were estimated from three harvest dates per location, one biological replication per harvest date, 10 sub-samples per harvest date for firmness, and three sub-samples per harvest for SS and TA.

| Cultivar | Firmness (g force) | SS (%) | Titrable Acids (g/100 ml) | SS/TA |
|---|---|---|---|---|
| UCD Royal Royce | 430.94 | 7.94 | 0.84 | 9.48 |
| Cabrillo | 359.61 | 8.05 | 0.77 | 10.50 |
| Monterey | 294.55 | 8.71 | 0.77 | 11.48 |

TABLE 7

Statistical significance (Pr > F) of differences between least square means for SS, TA, and SS/TA for 'UCD Royal Royce', 'Monterey', and 'Cabrillo' tested in unreplicated large-plot yield trials in five locations in 2017-18.

| | Soluble Solids Concentration (SS) | | Titratable Acids Concentration (TA) | | SS/TA | |
|---|---|---|---|---|---|---|
| Comparison | Least Square Mean Difference (%) | Pr > F | Least Square Mean Difference (g/100 ml) | Pr > F | Least Square Mean Difference | Pr > F |
| UCD Royal Royce-Monterey | −0.77 | 0.0405 | 0.07 | 0.0090 | −2.00 | <0.0001 |
| UCD Royal Royce-Cabrillo | −0.11 | 0.7808 | 0.06 | 0.0231 | −1.02 | 0.0185 |

TABLE 8

Least-square means (LSMs) for fruit weight (g/clamshell), soluble solids concentration (SS), fruit brightness, liquid leakage, and mold formation for 'UCD Royal Royce', 'Monterey', and 'Cabrillo' grown in four locations 2017-18 and stored for zero to 21 days postharvest. LSMs were estimated from two harvest dates per location

| Cultivar | Days Post-Harvest Storage | Weight (g/clamshell) | Soluble Solids (%) | Bright-ness | Liquid Leakage (g) | Mold (%) |
|---|---|---|---|---|---|---|
| UCD Royal Royce | 0 | 555.7 | 7.3 | 1.0 | 0.0 | 0.0 |
| Cabrillo | 0 | 555.4 | 7.5 | 1.3 | 0.0 | 0.0 |
| Monterey | 0 | 572.0 | 9.2 | 1.2 | 0.0 | 0.0 |
| UCD Royal Royce | 7 | 538.0 | 7.6 | 2.1 | 0.2 | 0.0 |
| Cabrillo | 7 | 538.7 | 7.4 | 2.0 | 0.2 | 0.0 |
| Monterey | 7 | 556.3 | 9.1 | 1.8 | 0.0 | 0.0 |
| UCD Royal Royce | 14 | 523.0 | 7.5 | 3.4 | 0.0 | 1.0 |
| Cabrillo | 14 | 522.9 | 7.3 | 3.3 | 0.8 | 1.2 |
| Monterey | 14 | 542.3 | 9.5 | 3.0 | 0.0 | 0.5 |
| UCD Royal Royce | 21 | 508.6 | 7.0 | 4.1 | 0.8 | 12.7 |
| Cabrillo | 21 | 504.4 | 7.3 | 4.3 | 35.8 | 36.7 |
| Monterey | 21 | 526.4 | 8.7 | 3.8 | 0.2 | 11.8 |

'UCD Royal Royce' produced fruit meeting or exceeding industry standards for mass-production cultivars (Tables 6-8). The fruit was firm, withstood the rigors of harvest, packing, and storage, and maintained acceptable fruit quality and appearance for over two weeks of storage. 'UCD Royal Royce' produced significantly firmer fruit than either 'Cabrillo' ($p<0.0001$) or 'Monterey' ($p<0.0001$). 'UCD Royal Royce' additionally had significantly lower SS concentration than 'Monterey' ($p<0.0001$), but was not significantly different compared to 'Cabrillo' ($p=0.78$). The SS/TA ration for 'UCD Royal Royce' was significantly lower than 'Monterey' ($p<0.0001$) and 'Cabrillo' ($p<0.019$).

'UCD Royal Royce' maintained adequate marketability and visual appeal over 14 days of post-harvest storage, the industry standard (Table 8), as did 'Cabrillo' and 'Monterey'. The marketability of fruit stored for 21 days post-harvest was inadequate for all three cultivars. Fruit weight and brightness significantly decreased as post-harvest storage time increased (Table 8). The fruit weight decreases were not significantly different among cultivars. Cultivar× post-harvest storage time interactions were only statistically significant for liquid leakage and mold formation, with 'Cabrillo' deteriorating more than 'UCD Royal Royce' and 'Monterey' (Table 8).

Disease Resistance Evaluation

'UCD Royal Royce' and additional cultivars were screened for resistance to *Fusarium* wilt, *Verticillium* wilt, *Macrophomina*, and *Phytophthora* crown rot in Davis, Calif. field experiments between 2015 and 2018. These included 2015-16 and 2016-17 *Fusarium* wilt screening experiments with 480 to 960 entries, a 2015-&b 16 *Macrophomina* experiment with 960 entries, 2016-17 and 2017-18 *Verticillium* wilt experiments with 480 to 960 entries, and a 2017-18 *Phytophthora* crown rot experiment with 480 entries. Entries were arranged in randomized complete blocks experiment designs with four single-plant replications per entry. The 2015-16 experiments were planted in virgin soil in Davis, Calif. The 2016-17 and 2017-18 experiments were planted in fumigated soils in Davis, Calif. For each experiment, plants were artificially inoculated with the respective pathogen and phenotyped for disease symptoms on an ordinal scale, where 1=highly resistant (symptomless), 2=resistant, 3=intermediate, 4=susceptible, and 5=highly susceptible (dead). Within each experiment, plants were phenotyped at six different time points to study changes in the phenotypic distributions and quantify the progression of disease symptoms over time.

'UCD Royal Royce' was susceptible to Fusarium wilt (4.5 on scale), moderately susceptible to *Verticillium* wilt (3.1 on scale), moderately susceptible to *Phytophthora* crown rot (3.3 on scale), and susceptible to *Macrophomina* (5.0 on scale).

BOTANICAL DESCRIPTION

The following botanical descriptors are characteristic of 'UCD Royal Royce'. The descriptors were collected from two different sites in May 2017 in Santa Maria, Calif. Colors are designated with reference to The Royal Horticultural Society (R.H.S.) Colour Chart, Sixth Edition, 2015. The characteristics of 'UCD Royal Royce' may vary in detail, depending upon environmental factors and culture conditions.

Growth habitat: Semi-upright Plant height average of 29 cm.
Plant spread average of 37 cm.
Density of foliage: Medium.
Vigor: Medium.
Position of inflorescence in relation to foliage: Same level.
Number of stolons: Average of 6.
Stolon, anthocyanin coloration: 60B.
Stolon, density of pubescence: Sparse.
Leaf size: Medium.
Leaf color: Adaxial 137A, Abaxial 147B.
Leaf blistering: Absent.
Leaf glossiness: Medium glossy.
Leaf variegation: Absent.
Terminal leaflet, length in relation to width: Average of 89 mm long and 77 mm wide.
Terminal leaflet, shape of base: Obtuse.
Terminal leaflet, margin: Serrate to crenate.
Terminal leaflet, shape in cross section: Concave.
Petiole, length: Average of 19 cm.
Petiole, attitude of hairs: Horizontal.
Stipule, anthocyanin coloration: Core color 144D, Margin color 144A (absent or very weak).
Inflorescence, number of flowers: Many.
Pedicel, attitude of hairs: Slightly outwards.
Pedicel, anthocyanin coloration: 60B.
Flower diameter: Average of 24 mm.
Flower, arrangement of petals: Touching.
Flower, size of calyx: Calyx diameter average of 33 mm.
Color of calyx: 137B.
Flower stamen: Present.
Number of stamens per flower: Average of 24.
Number of sepals per flower: Averages of 12.
Petal, length in relation to width: Equal, Average of 10 mm long and 9.5 mm wide.
Petal, color of upper side: NN155B.
Petal color of lower side: NN155B.
Number of petals per flower: Average of 6.
Fruit, length in relation to width: Average of 45 mm long and 39 mm wide.
Fruit size: Average of 30 grams through the season for both primary and secondary fruit.

Fruit shape: Conical.
Fruit, difference in shape of terminal and other fruits: None or very slight.
Fruit color: N45B.
Fruit, evenness of color: Even or very slightly uneven.
Fruit glossiness: Medium.
Fruit, evenness of surface: Even or very slightly uneven.
Fruit, width of band without achenes: Absent or very narrow.
Fruit, positions of achenes: Below surface.
Achene color: 4A.
Fruit, position of calyx attachment: Inserted.
Fruit, attitude of sepals: Upwards.
Fruit, diameter of calyx in relation to fruit diameter: Slightly larger.
Fruit, adherence of calyx: Strong.
Fruit firmness: Very firm.
Fruit, color of flesh (excluding core): 40C.
Fruit, color of core: 37A.
Fruit cavity: Average of 6 mm.
Time of beginning of flowering: Medium, starts in February to November.
Time of beginning of fruit ripening: Medium, starts in March to December.
Type of bearing: Day neutral.

PLANT AND FOLIAGE COMPARISONS

Fruiting plants of 'UCD Royal Royce' are similar in height to 'Monterey', but slightly taller than 'Cabrillo' and 'San Andreas'. The spread is more compact than 'Monterey' and 'Cabrillo' and more similar to 'San Andreas'. Leaves (including petioles) for 'UCD Royal Royce' are longer than for all three comparative cultivars. Color for the upper and lower levels of the leaves of 'UCD Royal Royce' are darker green than all 3 comparative cultivars. Serrations at mid-season are more pointed than Monterey and more similar in shape and number to 'Cabrillo' and 'San Andreas'. The stipule length of 'UCD Royal Royce' is shorter than all three comparative cultivars. Stolon production of 'UCD Royal Royce' is similar to 'San Andreas', but less than for 'Cabrillo' and 'Monterey'.

FLOWERING AND FRUITING COMPARISONS

'UCD Royal Royce' is similar to other California day-neutral cultivars (e.g. 'Cabrillo', 'Monterey' and 'San Andreas') in that it will flower independently of day length, given appropriate temperature and horticultural conditions. The primary flowers for 'UCD Royal Royce' are similar in size to the comparative cultivars with a calyx that is distinctly larger relative to the corolla on the primary fruit. The sepals for 'UCD Royal Royce' are slightly longer and wider than all 3 comparative cultivars. The calyx of 'UCD Royal Royce' is variable (reflex to flat) more similar to 'Monterey' and 'San Andreas', less reflexive than 'Cabrillo'. The fruit shape of 'UCD Royal Royce' can vary through the season, but is generally a conic fruit as compared to the long conic fruit of 'San Andreas', the short and rounded conic fruit of 'Cabrillo' and the short and slightly flattened conic fruit of 'Monterey'. External fruit color of 'UCD Royal Royce' is darker red than for 'Monterey' and 'Cabrillo'. The internal fruit color of 'UCD Royal Royce' is lighter than both 'Monterey' and 'Cabrillo'.

Achenes of 'UCD Royal Royce' are slightly indented in the fruit, comparatively similar to the fruit of 'Cabrillo' and 'San Andreas', whereas 'Monterey' has more flat to the surface position.

What is claimed is:

1. A new and distinct cultivar of strawberry plant having the characteristics substantially as described and illustrated herein.

* * * * *